United States Patent [19]
Goldfarb

[11] Patent Number: 5,596,986
[45] Date of Patent: Jan. 28, 1997

[54] BLOOD OXIMETER

[75] Inventor: David Goldfarb, Burke, Va.

[73] Assignee: Scico, Inc., Annapolis, Md.

[21] Appl. No.: 18,349

[22] Filed: Feb. 16, 1993

Related U.S. Application Data

[63] Continuation of Ser. No. 769,153, Sep. 27, 1991, abandoned, which is a continuation of Ser. No. 324,939, Mar. 17, 1989, abandoned.

[51] Int. Cl.$^6$ .................................................. A61B 5/00
[52] U.S. Cl. ........................ 128/633; 128/637; 356/41
[58] Field of Search ..................... 128/633, 634, 128/637; 606/2, 3; 356/39–41, 364, 367; 607/88, 89

[56] References Cited

U.S. PATENT DOCUMENTS

| | | | |
|---|---|---|---|
| 3,461,856 | 8/1969 | Polanyi | 128/2 |
| 3,511,227 | 5/1970 | Johnson | 128/2 |
| 3,704,706 | 12/1972 | Herezfeld et al. | 128/2 |
| 3,748,484 | 7/1973 | Covault | 356/364 |
| 3,825,342 | 7/1974 | Lubbers et al. | 356/41 |
| 3,963,019 | 6/1976 | Quandt | 128/633 |
| 4,086,915 | 5/1978 | Kofsky et al. | 128/2 |
| 4,253,723 | 3/1981 | Kojima et al. | 369/104 |
| 4,394,572 | 7/1983 | Wilber | 250/239 |
| 4,407,290 | 10/1983 | Wilber | 128/633 |
| 4,444,498 | 4/1984 | Heineman | 356/246 |
| 4,447,150 | 5/1984 | Heineman | 356/41 |
| 4,523,279 | 6/1985 | Sperinde et al. | 364/416 |
| 4,598,715 | 7/1986 | Machler et al. | 128/634 |
| 4,603,700 | 8/1986 | Nichols et al. | 128/633 |
| 4,623,248 | 11/1986 | Sperinde | 356/41 |
| 4,650,327 | 3/1987 | Ogi | 356/243 |
| 4,655,225 | 4/1987 | Dahne et al. | 128/633 |
| 4,684,245 | 8/1987 | Goldring | 356/41 |
| 4,697,593 | 10/1987 | Evans et al. | 128/634 |
| 4,723,554 | 2/1988 | Oman et al. | 128/664 |
| 4,763,282 | 8/1988 | Rosenberg | 364/524 |
| 4,773,422 | 9/1988 | Isaacson et al. | 128/633 |
| 4,809,340 | 2/1989 | Mersereau | 350/162.13 |
| 4,865,406 | 9/1989 | Khanarian et al. | 350/96.34 |
| 4,936,679 | 6/1990 | Mersch | 356/41 |

OTHER PUBLICATIONS

"Influence of Oxygen Saturation, Erythrocyte Concentration and Optical Depth Upon the Red and Near–Infrared Light Transmittance of Whole Blood", Kurt Kramer et al., pp. 229–246.

"A Single–blind Study of Pulse Oximetry in Children", Anesthesiology, Coté, et al., V. 68, No. 2, Feb. 1988, pp. 184–188.

"Accuracy and reliability of pulse oximetry in premature neonates with respiratory distress", Ginny W. Henderson, Journal of the American Association of Nurse Anesthetists, Jun. 1988/vol. 56/No. 3, pp. 224–228.

"Accuracy of Pulse Oximetry During Arterial Oxyhemoglobin Desaturation in Dogs", Anesthesiology, Sendak, V. 68, No. 1, Jan. 1988, pp. 111–114.

"Methylene Blue and Indocyanine Green Artifactually Lower Pulse Oximetry Readings of Oxygen Saturation. Studies in Dogs". Avner Sidi, M. D. et al., Journal of Clinical Monitoring, vol. 3, No. 4, Oct. 1987, pp. 249–256.

"Pulse Oximetry Fails to Accurately Detect Low Levels of Arterial Hemoglobin Oxygen Saturation in Dogs", Avner Sidi, M. D., et al., Journal of Clinical Monitoring, vol. 3, No. 4, Oct. 1987, pp. 257–262.

"Transcutaneous Oxygen Monitoring during Fiberoptic Bronchoscopy", Maimona B. Ghows, MD, Chest/89/4/Apr. 1986, pp. 543–544.

(List continued on next page.)

Primary Examiner—David M. Shay
Attorney, Agent, or Firm—David Newman & Associates, P.C.

[57] ABSTRACT

A backscatter type non-invasive blood oximeter utilizes a coherent, polarized and tuneable monochromatic light source to measure parameters related to blood oxygen content. A microprocessor calculates information related to blood oxygen content from the sensed information and a display system displays the blood oxygen content.

14 Claims, 7 Drawing Sheets

OTHER PUBLICATIONS

"Measurement of Pulsatile Blood Flow", Donald L. Fry, MD, IRE Transactions on Medical Electronics, Dec. 1959, pp. 259–266.

"Indirect Measurement of Instantaneous Arterial Blood Pressure in the Human Finger by the Vascular Unloading Technique", K. Yamakoshi et al., IEEE Transactions on Biomedical Engineering, vol. BME–27, No. 3, Mar. 1980, pp. 150–155.

"New oscillometric method for indirect measurement of systolic and mean arterial pressure in the human finger, Part 1: model experiment", Yamakoshi et al., Med. & Biological Engineering & Computing, May 1982, pp. 307–313.

"New oscillometric method for indirect measurement of systolic and mean arterial pressure in the human finger. Part 2: correlation study", K. Yamakoshi et al., Med. & Biological Engineering & Computing, May 1982, pp. 314–318.

"Special Communications, A plethysmographic method for determination of flow ad volume pulsations in a limb", Dahn, et al., Journal of Applied Physiology, vol. 28, No. 3, Mar. 1970, pp. 333–336.

"Plethysmographic in vivo determinations of elastic properties of arteries in man", Dahn et al., Journal of Applied Physiology, vol. 28, No. 3, Mar. 1970, pp. 328–332.

"Pulse Oximetry: Physical Principles, Technical Realization and Present Limitations", Michael R. Neuman, Dept. of Reproductive Biology, Casa Western Reserve University, Cleveland, Ohio, pp. 135–144.

"Thermal injury associated with pulse oximetry", J. Bannister, Royal Infirmary, pp. 424–425.

"The Accuracy and Response Characteristics of a simplified ear Oximeter", Rebuck, MD, et al., A Simplified Ear Oximeter, CHEST/83/6/Jun. 1983, pp. 860–864.

"ACCP Scientific Section Recommendations, Noninvasive Monitoring of Arterial Blood Gases", Burki et al., CHEST/83/4/Apr. 1983, pp. 666–670.

"Pulse Oximetry—principle and first experiences during anesthesia", Dorlas et al., Acta Anasthesologica Belgica, 1987, 38.No. 2, pp. 133–137.

"New Methods For Whole Blood Oximetry", Schmitt et al., Annals of Biomedical Engineering, vol. 14, pp. 35–52, 1986.

"Changing Perspectives in Monitoring Oxygenation", Anesthesiology, H. Barrie Fairley, V 70, No. 1, Jan. 1989, pp. 2–4.

"Pulse Oximetry", Tremper, MD, et al., Anesthesiology, 70, pp. 98–108, 1989.

"The current status of pulse oximetry", Taylor, et al., Anaesthesia, 1986, vol. 41, pp. 943–949.

"Pulse Oximetry, Monitoring Arterial Hemoglobin Oxygen Saturation", Bland, AORN Journal, Apr. 1987, vol. 4, pp. 964–965 & 967.

"A microcomputer oximeter for whole blood", Kiel et al., 1983 the American Physiological Society, pp. H722–H725.

"History, Status and Future of Pulse Oximetry", John Severinghaus, Dept. of Anesthesia, Univ. of Calif., San Francisco, Ca, pp. 3–8.

"Multiple Scattering of Waves and Optical Phenomena", Twersky, Journal of the Optical Society of America, vol. 52, No. 2, FEB 1962, pp. 145, 148–171.

"Role of Light Scattering in Whole Blood Oximetry", Steinke, et al., IEEE Transactions on Biomedical Engineering, vol. BME–33, No. 3, Mar. 1986, pp. 294–303.

"Absorption and Multiple Scattering by Biological Suspensions", Twersky, Math. Dept. & Center for Advanced Study, Univ. of Illinois, vol. 60, pp. 1084–1093.

"Interface Effects in Multiple Scattering by Large, Low-Refracting, Absorbing Particles", Twersky, Journal of the Optical Society of America, vol. 60, No. 7, Jul. 1970, pp. 908–914.

"Range of Accuracy of Two Wavelength Oximetry", Chapman et al., CHEST/89/4/Apr. 1986, pp. 540–542.

"Comparison of Blood Pressure Measurement by Doppler and by Pulse Oximetry Techniques", Wallace et al., The Intn'l Anesthesia Research Society, 1987;66, pp. 1018–1019.

"Analysis of vessel absorption profiles in retinal oximetry", Roberts, Medical Physics, vol. 14, No. 1, Jan./Feb. 1987, pp. 124–130.

"Use of Pulse Oximetry As a noninvasive Indicator of Intravascular Volume Status", Partridge, Journal of Clinical Monitoring, vol. 3, No. 4, Oct. 1987, pp. 263–268.

"Estimation of Oxygen Utilization by Dual Oximetry", Rasanen et al., Ann. Surg., Nov. Year?, vol. 306, No. 5, pp. 621–623.

"Effect of Nail Polish on Pulse Oximetry", Coté et al., Intn'l Anesthesia Research Society, 1988, pp. 683–686.

"The Use of Cutaneous Oximetry in the Prescription of Long–term Oxygen Therapy", Carlin et al., CHEST/94/2/Aug. 1988, pp. 239–241.

"Is Routine Assessment of Arterial Oxygen Saturation in Pulmonary Outpatients Indicated?", Loggan, CHEST/94/2/Aug. 1988, pp. 242–244.

"Validity of Ear oximetry in Clinical Exercise Testing", Hansen, et al., CHEST/91/3/Mar. 1987, pp. 333–337.

"Critical incidents detected by pulse oximetry during anaesthesia", McKay et al., Canadian Journal of Anaesthesia, pp. 265–269.

"What Difference Does Pulse Oximetry Make?, The Journal of Anesthesiology", Cohen, et al., vol. 68, No. 2, Feb. 1988, pp. 181–183.

"Oximetry—Know Thy Limits, Dept. of Medicine", Andrew L. Ries, Albert Einstein College of Medicine, Bronx, NY., Editorials, p. 316.

"A Simple Method to Prevent Interference with Pulse Oximetry by infrared Heating Lamps", Alan D. Zablocki, Letters to the Editor, ANESTH ANAGL. 1987; 66, p. 915.

"Routine Oximetry, A Fifth Vital Sign?", Thomas A. Neff, CHEST/94/2/Aug. 1988, p. 227.

"Safe anaesthesia: pulse oximetry for all?", J. Edmonds-Slal, The Radcliffe Infirmary, p. 603, and Pulse oximetry for all?, M. J. Biggart, Royal Victoria Infirmary, pp. 603–604.

"Noninvasive versus Invasive Doppler Renal Blood Velocity and Flow Measurements", Greene et al., IEEE Transactions on Biomedical Engineering, vol. BME–33, No. 3, Mar. 1986, pp. 302–307.

"Pulse oximetry: A new technology to assess patient oxygen needs in the neonatal intensive care unit", Riedel, The Journal of Perinatal and Neonatal Nursing, Jul. 1987, pp. 49–57.

BLOOD OXIMETER

This is application is continuation of application Ser. No. 07/769,153, filed Sep. 27, 1991, now abandoned, which is a continuation of application Ser. No. 07/324,939, filed Mar. 17, 1989, now abandoned.

BACKGROUND OF THE INVENTION

1. Field of the Invention

This invention relates to the field of blood oximetry. More particularly it relates to an improved optical blood oximeter which non-invasively measures blood oxygen content by backscattered light.

2. Description of Related Art

1. Theory

The basic concepts of optically based oximetry were described in the early 1930's and expanded in the 1940's in the works of Nicolai [L. Nicolai, Uber Sichtbarmachung, Verlauf and Chemische Kinetik der Oxyhemoglobinreduktion im Lebenden Gewebe, Besonders in der Menschlichen Haut, *Arch. Gesamte Physiol.* 229: 372 (1932)] and Kramer [K. Kramer, Ein Verfahren zur Fortlaufenden, Messung des Sauerstoffgehalets im Stromenden Blute en Uneroffneten Gefassen, *Ziet. f. Bilogie.* 96: 61 (1935)] and Matthes [K. Matthes, Untersuchungen uber die Sauerstoffsaptingung des Menschlichen Arterienblutes, *Arch. f. Exper. Path, U Pharmakel.* 179: 698 (1935)] respectively. These early methodologies were based upon measuring the difference in the optical transmission spectrum of oxygenated and deoxygenated hemoglobin. The measurements were made at the isobestic point of hemoglobin and the point of maximum transmission ($HbO_{max}$). $HbO_{max}$ is that frequency which is maximally affected by changes in the oxygen content of hemoglobin. It is typically 660 nanometers ("nm"). By knowing the relative intensities of red and infrared sources, it was possible to use the Lambert-Beer law to determine the relative amount of hemoglobin in solution and its oxygenation state. A complete derivation of the theory is presented below:

The Lambert-Beer law is stated as:

$$I(t)=I(o)\exp^{(-acd)} \quad \text{(Equation 1)}$$

where:

$I(t)$=Intensity of transmitted light
$I(o)$=Source intensity
$a$=molar absorption coefficient (sample)
$c$=concentration (sample)
$d$=optical path length If the Lambert-Beer law is restated as a function of optical density (OD), equation (1) becomes:

$$OD=\log(20)I(o)/I(t)=acd \quad \text{(Equation 2)}$$

If the path length is held constant and measurements are carried out at widely spaced wavelengths, then equation (2) becomes:

$$OS=A-B(OD1/OD2) \quad \text{(Equation 3)}$$

where:

OS=Oxygen saturation
A=Constant (experimentally determined)
B=Constant (experimentally determined)
OD1=Optical density at $HbO_{max}$ (lambda red)
OD2=Optical density at isobestic point (lambda IR)

In 1935, an ear oximetry device was described [K. Matthes, Untersuchungen uber die Sauerstoffsaptingung des Menschlichen Arterienblutes, *Arch. f. Exper. Path, U Pharmakel.* 179: 698 (1935)] that employed the transmission theory described by Equation (3). The device was prone to errors due to skin pigmentation and the optical properties of whole blood. Also, for the data to be valid, the skin had to be heated to approximate arterial blood.

If we examine what happens to light entering a hemoglobin solution we find that it has three components: transmission, absorption, and reflection. Application of the Lambert-Beer law for the case of reflection and application of the principles used in the derivation of equation (3) yield:

$$OS=C-D(X2/X1) \quad \text{(Equation 4)}$$

where:

C=Constant (experimentally determined)
D=Constant (experimentally determined)
X1=Optical density at $HbO_{max}$ (lambda red)
X2=Optical density at isobestic point (lambda IR)

In 1944, Drabkin [D. L. Drabkin and C. F. Schmidt, Spectrophotometric Studies XII. Observation of Circulating Blood In Vitro and the Direct Determination of the Saturation of Hemoglobin in Arterial Blood, *J. Biol. Chem.* 157: 69 (1944)] demonstrated an invasive device that gave very good results when compared against gasometric analyses. A non-invasive device was demonstrated in 1949 [R. Brinkman, W. G. Zijistra and R. K. Koopmans, A Method for Continuous Observation of Percentage Oxygen Saturation in Patients *Arch. Chir. Neeri.* 1:333 (1949)] that also correlated well with gasometric analyses, but suffered from problems in repeatability across pigmentation and tissue types. In 1980 a multispectral device was developed [S. Takatani, P. W. Cheung and E. A. Ernst, A Noninvasive Tissue Reflectance Oximeter, *Ann. Biomed. Engrg.* 8: 1 (1980)] that addressed the pigmentation problem but still suffered from other problems related to path length resolution.

A new measurement technique was introduced in 1980 for the determination of oxygen saturation [I. Yoshiya, Y. Shimada and K. Tanaka, Spectrophotometric Monitoring of Arterial Oxygen Saturation in the Fingertip, *Med. Biol. Engrg. & Comput.* 18: 27 (1980)]. The measurement looks at the variation of optical density as a function of variations in blood volume during the cardiac cycle, hence the name pulse oximetry. The unique feature of this device is its ability to look at arterial blood without the necessity of heating the skin. This ability arises because the calculations are based on capillary blood volume variations resulting during the cardiac cycle. During systole, a fresh bolus of blood infuses the capillary bed increasing the blood volume and hence the optical density. During diastole, the venous runoff will decrease the volume with an attendant decrease in optical density. Since the optical density change at the isobestic point is the same from pulse to pulse and the optical density will change at $HbO_{max}$ with variations in oxygen saturation, equation (3) expresses the transmission case and equation (4) the reflection case.

2. Technology

According to Neuman [Michael R. Neuman, Pulse Oximetry: Physical Principles, Technical Realization and Present Limitations], commercially available non-invasive devices consist primarily of the transmission type. They usually consist of the following components:

1. Probe—contains the light sources and detector diode;

2. Amplifier—used to magnify the signal received (via electric cable) from the probe;
3. Filters—used to remove extraneous noise and to compensate for movement artifact;
4. Power Supply—provides power to the probe, amplifiers, processor electronics, and display electronics;
5. Processor electronics—convert the analog signal (from the probe) into a digital signal for processing by various algorithms. Usually consists of a micro computer and various proprietary software tools; and
6. Display Electronics—Cathode ray tube and electronics necessary to display the information to the user.

Figure 1:
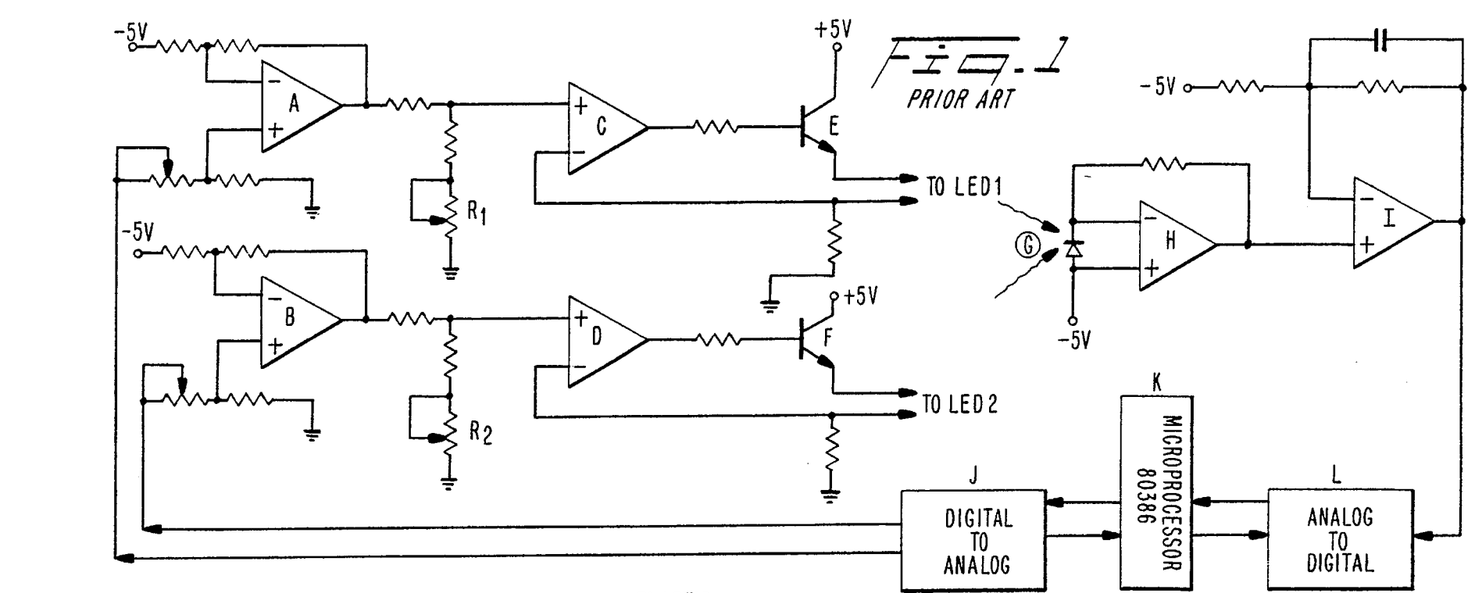
FIG. 1 is a schematic diagram of a typical prior art blood oximeter.
Figures 2A, 2B:
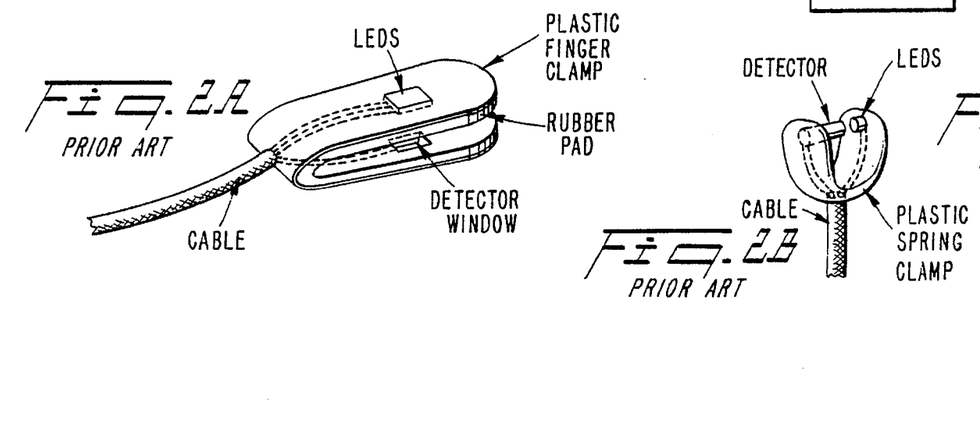
FIG. 2A is a drawing of a typical prior art transmission-type blood oximeter sensor.
FIG. 2B is a drawing of a typical prior art transmission-type blood oximeter sensor for use on an ear.
Figure 2C:
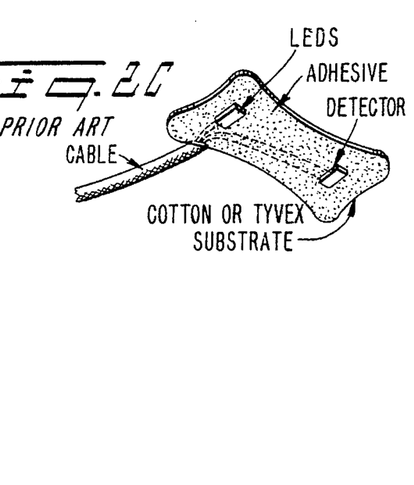
FIG. 2C is a drawing of a typical prior art transmission-type blood oximeter sensor for use on a nose.
Figures 3, 4A:
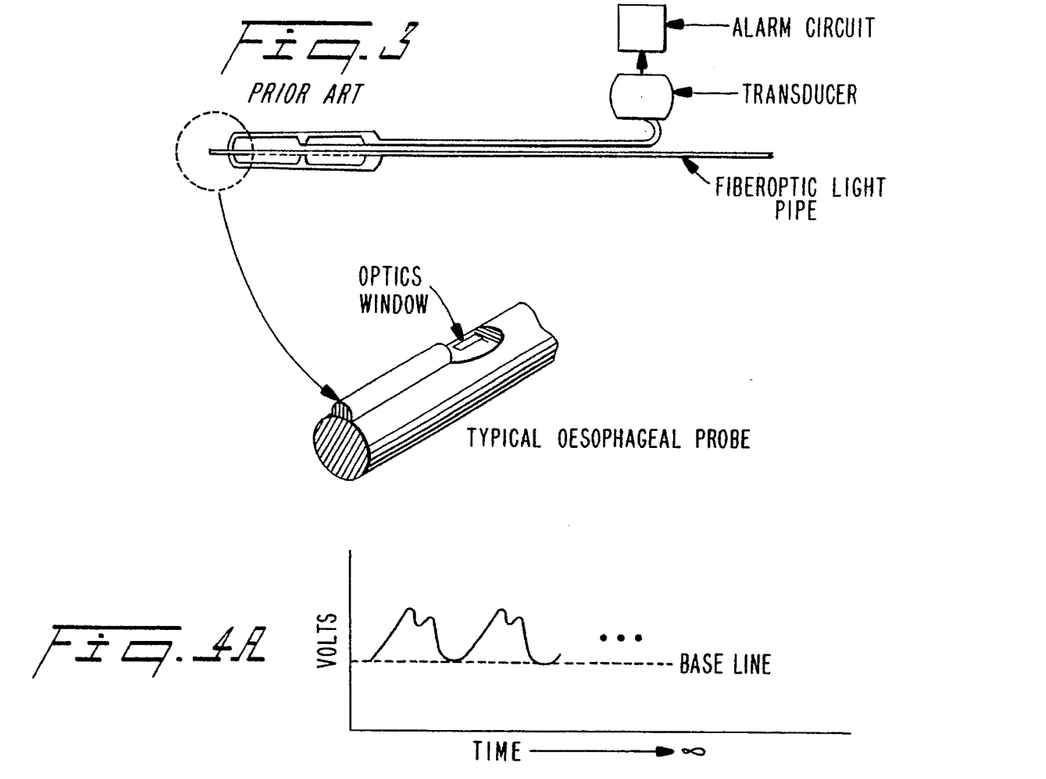
FIG. 3 is a drawing of a typical prior art reflection-type blood oximeter sensor for use in the oesophageal airway.
FIG. 4A is a typical signal trace of a "clean" plethysmographic signal.

FIG. 1 depicts the arrangement of these components in the majority of commercially available prior art devices. The components depicted are common to both transmissive and reflection devices. FIGS. 2A, 2B and 2C depict the arrangement of the probes of several prior art transmissive devices. FIG. 3 depicts a prior art reflection-type blood oximeter sensor for use in the oesophageal airway.

3. Operation

Most commercially available pulse oximeters are microprocessor controlled. Software in the computer directs the sequencing of events such as turning on the various light sources and then reading the transmitted intensity of either infrared or red light. Once the intensities are known, the microprocessor is then tasked with performing several table look ups and fitting the data to the following equation:

$$SO_2 = a(A*LAMBDA1/A*LAMBDA2) + b \quad \text{(Equation 5)}$$

where:

$$a = extLAMBDA2Hb/(extLAMBDA2Hb - extLAMBDA1HbO) \quad \text{(Equation 6)}$$

and $$b = extLAMBDA1Hb/(extLAMBDA1Hb - extLAMBDA1HbO) \quad \text{(Equation 7)}$$

The extinction coefficients are experimentally determined parameters that are dependent upon the particular devices (LEDs), wavelengths, and half-intensity bandwidths of the narrowband light sources. Processing for the values of a and b are the source of most of the table look-ups.

Operational amplifiers A, B, C, and D are used to amplify the signals coming from the two channels of the digital to analog converter (component J of FIG. 1). Amplifiers C and D are also used to adjust the cut-off point of the LEDs via the fine adjustment of resistors R1 and R2 respectively.

When either of the LEDs is on, the light passes through the sample and is measured by the PIN diode (component G of FIG. 1) and is then translated into a digital signal via the analog to digital converter (component L of FIG. 1). When the translation is completed, the resultant number is stored in the computer for later processing.

Figure 4B:
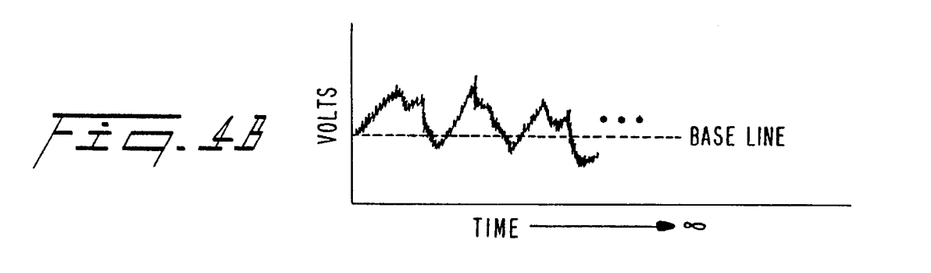
FIG. 4B is a typical signal trace of a plethysmographic signal subject to ambient light contamination.
Figure 4C:
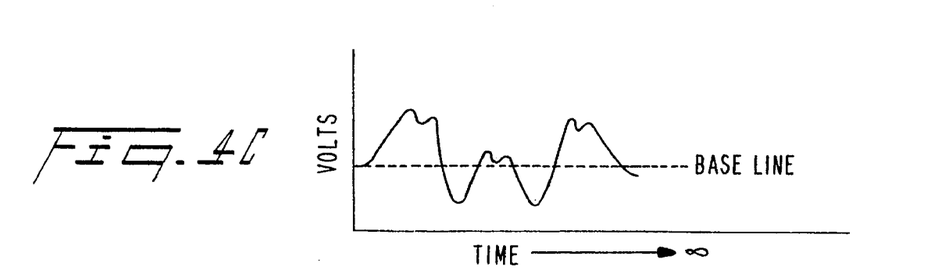
FIG. 4C is a typical signal trace of a plethysmographic signal subject to movement artifact.

Besides processing the plethysmographic signals, the microprocessor is also responsible for the processing required to remove movement artifacts, temperature drifts, and ambient light noise signals. FIG. 4 depicts how the noise and artifact signals combine to affect the plethysmographic signal.

4. Problems

Transmissive devices require the capability to transilluminate a group of vessels and are thereby restricted to locations on the periphery of circulation. The measurement is susceptible to errors when using vasoconstrictors or when a patient is in shock, i.e., poor peripheral perfusion. There are other sources of error:

a. optical path differences due to probe position/tissue volume changes;
b. path differences due to motion of probe relative to tissue;
c. differences in spectral characteristics of LEDs of the same type makes repeatability of readings from machine to machine difficult;
d. divergence from optical density versus lambda curves due to wide bandwidth of LEDs leads to erroneous saturation determinations; and
e. optical misalignment of sensor vs. detector makes sensitivity to hematocrit concentration critical.

Reflective devices also suffer from several problems:

a. depth of penetration and subsequent "blurring" of the intensity curves and refractive index shifts at connective tissue interfaces;
b. size of invasive devices makes them impractical; and
c. inability to resolve the source of the backscattered light leads to processing errors and deviations in values of Oxygen saturation measured by a pulse oximeter versus invasive measurement techniques.

There are mechanical problems associated with prior art devices. In instances where perfusion is poor or in cases involving neonates, the temperature rise associated with contact with the LEDs has led to cases of first and second degree burns [J. Bannister, D. H. T. Scott, Thermal Injury Associated With Pulse Oximetry, *Anaesthesia.*].

Neuman [Michael R. Neuman, Pulse Oximetry: Physical Principles, Technical Realization and Present Limitations] established the need for an improved pulse oximeter when he wrote the following:

"Although the pulse oximeter has achieved the status of routine use in many clinical settings, there are several areas where research on improvements of the technique is under way or needs to be encouraged. Noninvasive tissue pulse oximeters in use today operate in the transmission mode, and so the number of tissue sites where the instrument can be applied are limited to structures that can be easily transilluminated such as the fingers or toes. These locations are often not the most desirable due to their being at the extreme periphery of the circulatory system and therefore first to be compromised in circulatory shock. These locations are also likely to encounter more motion, and hence, more motion artifact than more central positions on the chest or abdomen. Historically it has been possible to look at in vitro oximetry from the backscatter (reflection) mode as well as the transmission. This step, however, has not been possible in practical noninvasive tissue oximeters. Research in understanding backscattered light from illuminated skin and subcutaneous tissue is necessary before practical instruments can be developed. Since light can penetrate deep in the body, one must be concerned about this depth of penetration, the effects of reflecting from subdermal tissue interfaces, and the sensitivity to local anatomy, and hence, the position of the sensor in such instruments."

"The availability of a practical backscatter oximeter would be an important development in that more locations would become available for clinical noninvasive oximetry. It would be possible to develop an intrapartum fetal pulse oximeter that could be used to monitor hemoglobin oxygen saturation in the fetal presenting part during labor and delivery. Although some investigators have made simultaneous recordings form transcutaneous oxygen sensors and pulse oximeters on the same subjects, the sensors had to be located at different sites due to their different location requirements. A backscatter mode pulse oximeter would make it practical to combine a transcutaneous $PO_2$ sensor and pulse oximeter into the same structure so that simultaneous measurements of oxygen tension and saturation could be made at the same site."

Having established the need for a backscatter device versus a merely improved transmissive device, it would be desirable for the new device to have the following attributes:

1. The new device shall be non-invasive;
2. Saturation readings taken with the device shall be independent of probe placement given a minimum tissue depth of approximately 2–3 millimeters;
3. The new device must account for or obviate the problems caused by index shifts at connective tissue interfaces;
4. The device should have improved repeatability and improved accuracy; and
5. The device should avoid burning tissue through long term exposure to high intensity light.

Satisfaction of requirements 1 and 2 rely on the development of a completely new approach to the measurement of the backscattered light intensity. One of the fundamental problems with backscattered light measurements and transmitted light measurements has been knowing (exactly) the properties of the reflecting or absorbing medium. To make the measurement process as independent of the physical properties of the absorbing/reflecting medium as possible requires extending the work of Twersky [Victor Twersky, Multiple Scattering of Waves and Optical Phenomena, *Journal of the Optical Society of America.* 52: 2 (1962)]. In his paper on the "Multiple Scattering of Waves and Optical Phenomena" he presents the general form for the phase change of the coherently reflected wave as:

$$v = \tan^{-1} \frac{|2I_m Z|}{|1 - |Z|^2|} \quad \text{(Equation 8)}$$

which is equal to 180 degrees whether the incident beam is parallel or perpendicularly polarized with respect to the incident plane. The coherent power reflection coefficient is stated by Twersky as:

$$R = |(1+Z)/(1-Z)|^2$$

Figure 5:
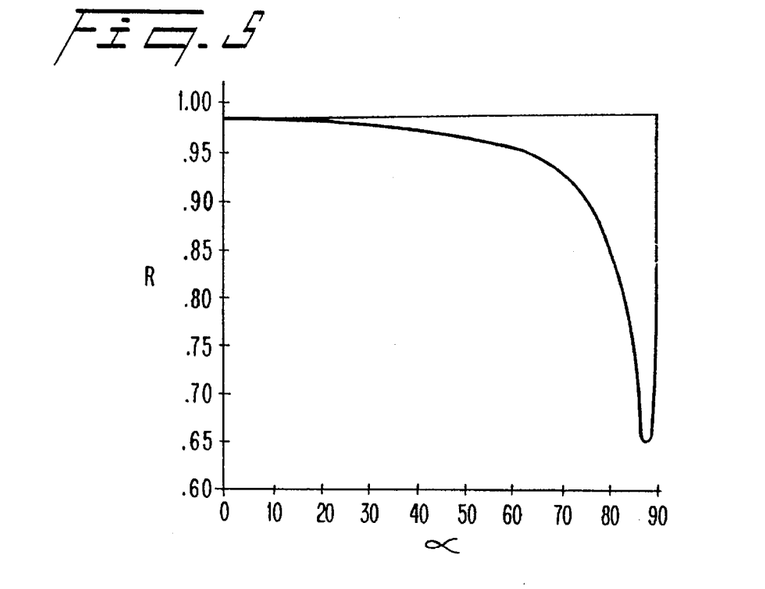
FIG. 5 is a trace of the coherent power reflection coefficient vs. angle of incidence.

FIG. 5 plots the coherent power reflection coefficient versus the angle of incidence with respect to the normal for parallel and perpendicularly polarized beams. We can see that as the parallel beam angle of incidence approaches 90 degrees the value of R approaches unity as does the perpendicular power reflection coefficient. The implication of equations 8 and 9 is that there should be an increase in sensitivity as a function of "grazing" angle, i.e., distance from source to receiver. This implication has been experimentally verified by Schmitt et al [J. M. Schmitt, F. G. Mihm, J. D. Meindl, New Methods For Whole Blood Oximetry, *Annals of Biomedical Engineering*, 14: 35 (1986)]. In the same study, it was also shown that the oxygen saturation measurement became more linear the closer the source was placed to the detector. The study also showed that as the source and detector separation increased there was a marked change in intensity (reflected power) as a function of hematocrit level.

The change in sensitivity as a function of source/receiver separation is due to the fraction of coherently reflected light into the forward versus backward half spaces [Victor Twersky, Multiple Scattering of Waves and Optical Phenomena, *Journal of the Optical Society of America.* 52: 2 (1962)]. LEDs, being essentially incoherent and non-polarized, will generate more reflected light into the forward half space than into the back half space. Therefore, as the grazing angle is reached they will appear to become more sensitive until the separation of the source and receiver causes the receiver's half angle to be exceeded and then no power is received.

The invention herein overcomes the drawbacks of the prior art by using a LASER as the source (polarized parallel to the incident plane) and a single mode monofilament light guide to deliver the light and gather the reflected light. By utilizing this system, the mathematical description of the system appears as if the source and detector are collocated. The byproduct of this apparent collocation is increased linearity and the coherently reflected fraction of the light approaches unity. The reason one polarizes the light parallel to the incident plane is to eliminate the sensitivity to hematocrit concentration which has been demonstrated by prior art reflection devices [J. M. Schmitt, F. G. Mihm, J. D. Meindl, New Methods For Whole Blood Oximetry, *Annals of Biomedical Engineering*, 14: 35 (1986)].

SUMMARY OF THE INVENTION

The present invention comprises a method and apparatus for non-invasively determining the blood oxygen content of a patient. Electromagnetic radiation (referred to herein as "light") (and which is both coherent and polarized in a preferred embodiment) form a tuneable narrowband electromagnetic radiation source such as a tuneable laser is projected into a patient and the backscattered light intensity is sensed. From the intensities of the backscattered light measured at a plurality of different frequencies the blood oxygen content is determined by a microprocessor carrying out preprogrammed calculations to solve for blood oxygen content as a function of predetermined coefficients and measured backscattered light intensities.

Accordingly, it is an object of this invention to provide an improved blood oximeter.

It is a further object of this invention to provide an improved method for determining the oxygen content of blood.

It is a further object of this invention to provide an improved non-invasive backscatter blood oximeter.

It is a further object of this invention to provide an improved non-invasive backscatter-type blood oximeter which makes use of a tuneable laser device to measure backscattered light intensity and thereby calculate blood oxygen content.

Other and further objects and advantages of the present invention will appear hereinafter.

DESCRIPTION OF THE PREFERRED EMBODIMENT

Figure 6A:
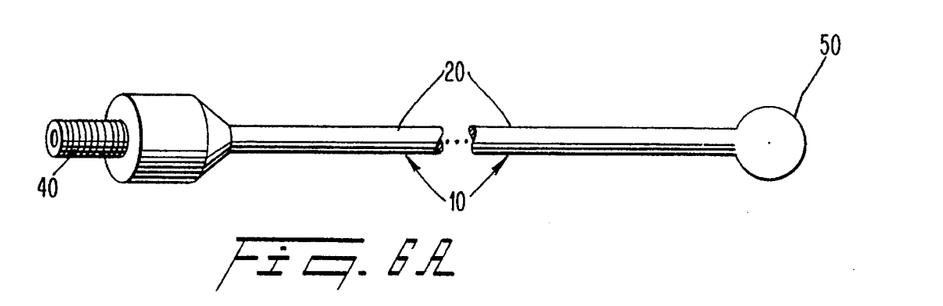
FIG. 6A is a diagram of a fiberoptic cable, connector and attachment interface according to a preferred embodiment of the present invention.

The present invention relates generally to a method and apparatus for measuring the oxygen content of blood.
Probe In a preferred embodiment of the present invention, a probe is attached to a patient whose blood oxygen content is to be measured. The probe is also attached to an optical bench and the optical bench is in turn connected to an electronics module which contains a microprocessor means and a display means together with other circuitry and software for performing the various functions of oximetry. Turning to FIG. 6A, a probe 10 is depicted according to a preferred embodiment of the present invention. The probe consists of a large diameter monofilament single mode fiberoptic cable 20 such as that available from Hewlett-Packard, which is attached to optical bench 30, a shown in FIG. 8, via a standard Hewlett-Packard 3/32 connector 40.

Figure 6B:
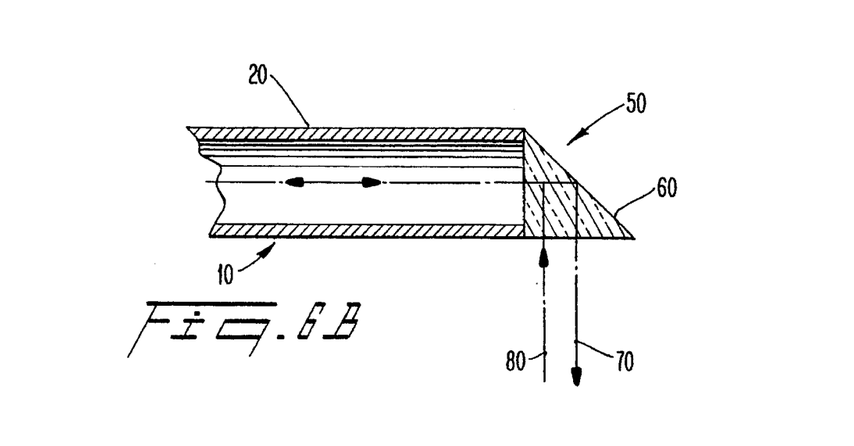
FIG. 6B is a cross-sectional diagram of a corner reflector attachment according to a preferred embodiment of the present invention.

The distal end 50 of probe 10 is comprised of a 90 degree corner reflector or prism 60. As shown in FIG. 6B, the prism 60 that is used to direct the incident light beam 70 into the sample and collect the backscattered light beam 80 from the sample. Incident light beam 70 and backscattered light beam 80 are substantially collinear although not depicted as such in FIG. 6B. Prism 60 is attached to fiberoptic cable 20 using optical grade cement as well known to those of ordinary skill in the art.

Prism 60 is not necessary in order to practice the invention and a fiberoptic cable could be terminated directly at the patient's skin. Prism 60 allows fiberoptic cable 20 to lie flat against the patient which is convenient in many situations.

Figure 7A:
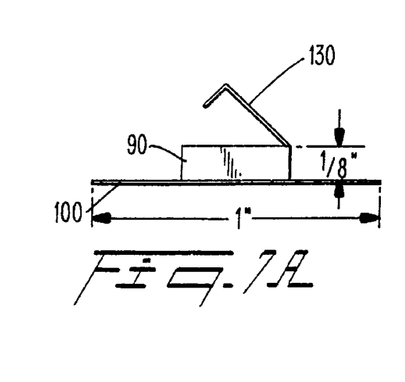
FIG. 7A is a side view of the annular attachment ring according to a preferred embodiment of the present invention.
Figure 7B:
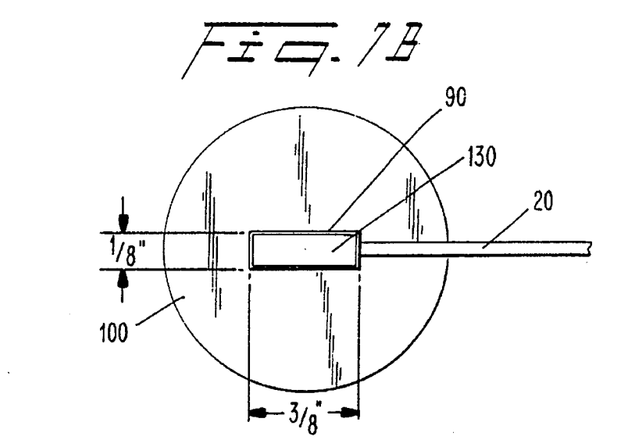
FIG. 7B is a top view of the annular attachment ring according to a preferred embodiment of the present invention.
Figure 7C:
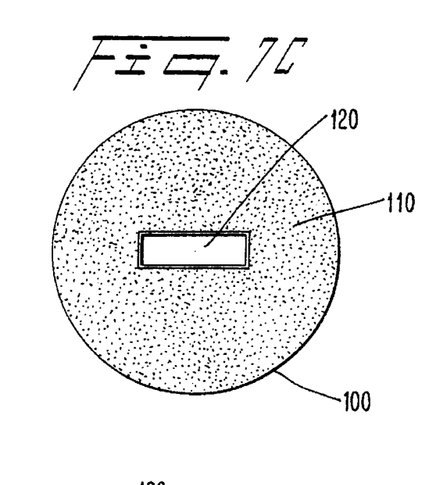
FIG. 7C is a bottom view of the annular attachment ring according to a preferred embodiment of the present invention.

Turning now to FIGS. 7A, 7B, 7C prism 60 is inserted into holder 90 which is a part of annular ring 100. Annular ring 100 may be constructed of a lightweight plastic and coated with hypo-allergenic adhesive 110 on the side which attaches to the patient. Incident light beam 70 and backscattered light beam 80 are directed through transparent window 120 in the annular ring 100. The attachment mechanism of this preferred embodiment employs the annular ring to stabilize torsional stresses which give rise to errors of the type discussed above. Fiberoptic cable 20 is secured in annular ring 100 via a hinged lid 130 that snaps securely into place thus anchoring distal end 50 within holder 90. In a preferred embodiment, transparent window 120 has dimensions of approximately 0.125 inch by 0.375 inch.

Optical Bench

Figure 8:
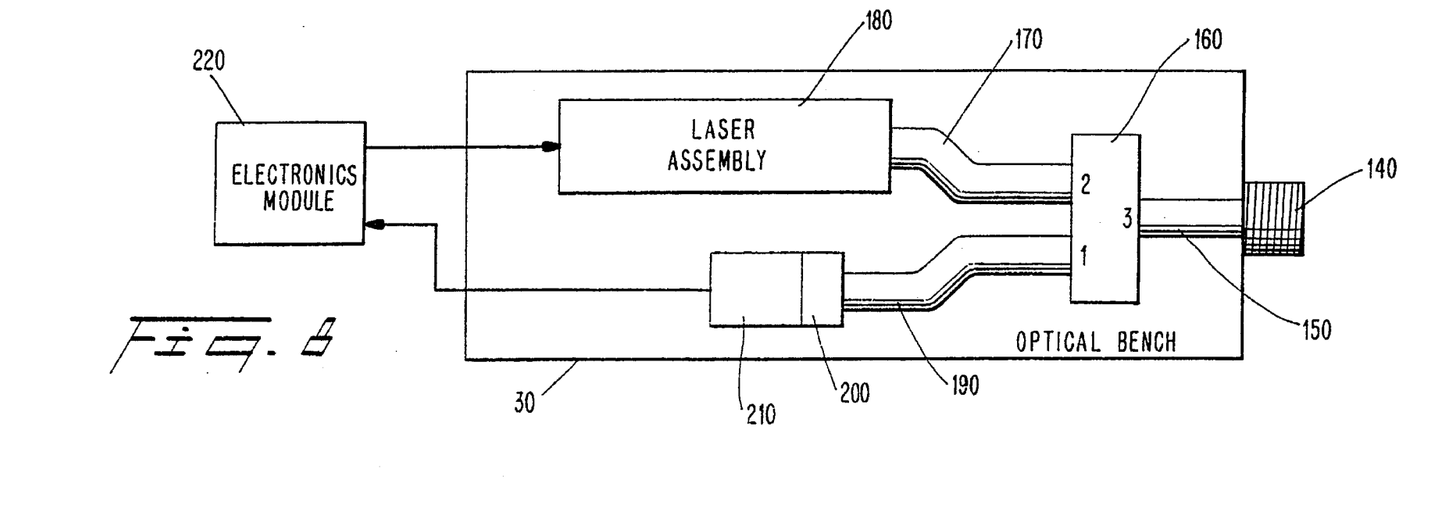
FIG. 8 is a schematic diagram of the optical bench according to a preferred embodiment of the present invention.

Optical bench 30 depicted in FIG. 8 comprises the structure which holds the transmitting and receiving components. To maintain dimensional stability over a wide range of temperatures, in a preferred embodiment of the present invention, the bench is constructed of 10 gauge titanium sheet. Other temperature stable materials could be used as known to those of skill in the art. In a preferred embodiment of the invention optical bench 30 is hermetically sealed in a container (not shown) and backfilled with an inert gas such as dry nitrogen or dry helium to reduce errors introduced by ageing of the optical components via environmental conditions. The size of the optical bench is determined by the type of tuneable laser chosen for a particular implementation. The type of tuneable laser will directly affect the size of the LASER assembly.

Optical bench 30 is connected to fiberoptic cable 20 by connector 140 which is adapted to receive connector 40 on fiberoptic cable 20. A fiberoptic pigtail 150 optically connects connector 140 and port 3 of directional coupler 160. Port 2 of directional coupler 160 is connected via fiber optic pigtail 170 to LASER assembly 180 which in turn is electrically coupled to electronics module 220. Port 1 of directional coupler 160 is connected via fiberoptic pigtail 190 to a polarizing filter 200. Polarizing filter is a linear polarizer 180° out of phase with the polarization of light emitted by LASER assembly 180. In this manner, unpolarized ambient light which did not come from LASER assembly 180 will be attenuated in attempting to pass through polarizing filter 200. PIN diode detector 210 is located adjacent polarizing filter 200 and is adapted to view the incoming backscattered light signal. In a preferred embodiment it is a wide band device sensitive to light in the range of approximately 500–1100 nm and is commonly available under the designation TRW OPT-100 from suppliers such as Arrow Electronics. PIN diode detector 210 is electrically connected to electronics module 220.

LASER assembly 180 is controlled and powered by electronics module 220. LASER assembly 180 is capable of generating coherent, polarized and monochromatic light of a plurality of different frequencies. LASER assembly 180 must therefore be either discretely tuneable or continuously tuneable.

According to the preferred embodiments, the LASER assembly can be implemented using at least any of the following devices:

1. A Titanium doped Sapphire paramagnetic ion laser (FIG. 9).
2. A progressively doped two dimensional LASER diode (FIGS. 10A and 10B).
3. A tuneable double Heterostructure LASER diode.
4. A series of selectable fixed frequency dye laser cells.
5. A doped fiberoptic cable pumped with a frequency doubled Nd:YAG laser exhibiting Raman scattering-type lasing where changes in the flexture of the cable are used to change the index of refraction of the cable and hence the frequency of the laser output.

The only restrictions on the laser assembly of the preferred embodiment are that the bandwidth of the laser chosen, i.e., the available frequencies, be wide enough to cover the range of approximately 600 to 1000 nanometers and that when a ramp voltage is applied the center frequency shifts linearly with increasing voltage. (Non-linear devices could be used if a suitable correction for the non-linearity were incorporated into the ramp voltage supply). This provides a wide range of precisely known frequencies that are correlated to the measured ramp voltage. This allows very precise determination of the transmitted light frequency and thereby eliminates the errors introduced when the transmitted frequency does not exactly correspond to the value used to empirically derive the data contained in the look-up tables used by the microprocessor (described later) to calculate the oxygen saturation. The laser's base center frequency is chosen such that it crosses the isobestic point (statistically determined for various tissue types). This reading, when taken in concert with the readings taken at the isobestic point for whole blood, will effectively compensate for the errors associated with skin pigmentation. A further description of the operation of the ARTIFACT program is contained below. The workings of the LASER assembly are described in detail below.

Electronics Module

Figure 13:
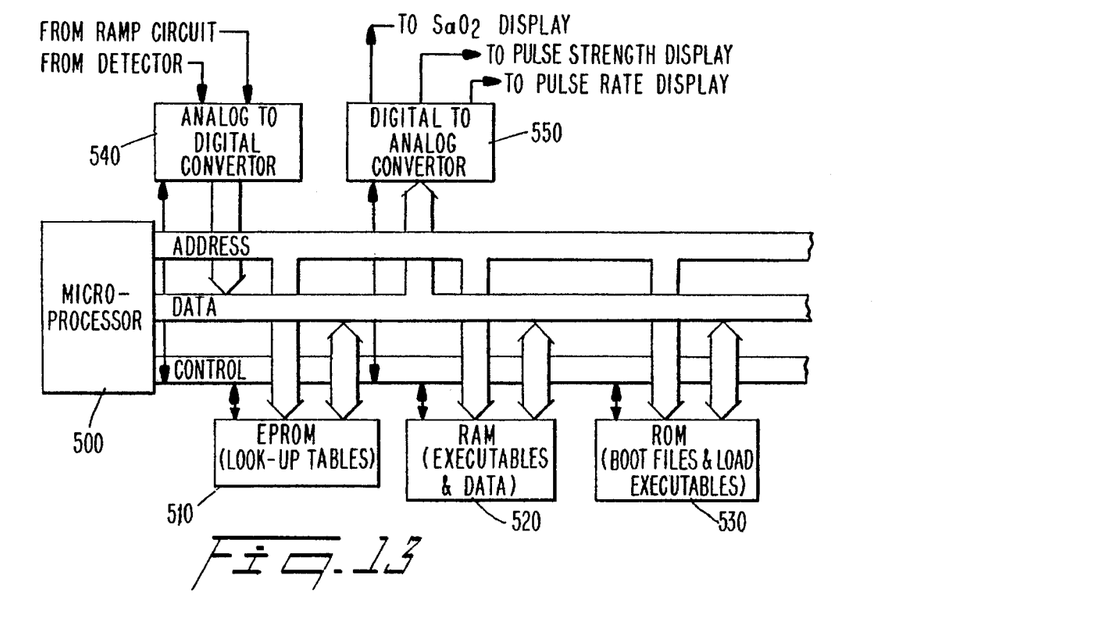
FIG. 13 is a block diagram of the signal processing system according to a preferred embodiment of the present invention.

As broadly depicted is FIG. 13, the electronics module of the present invention is composed of the circuitry necessary to provide the ramp voltage and power to the laser assembly and to perform the signal processing and control the display. The signal processing circuit consists of a flash analog to digital converter 540 that supplies digitized data to the microprocessor 500.

A "flash" analog to digital converter ("ADC") uses a brute force approach to digitization of an analog waveform. The input stage is constructed of a ladder circuit to which a voltage is applied. This will cause some of the comparators in the ladder circuit to turn on. The sum of the voltages from the comparators is "hard wired" to certain digital outputs, such that a voltage sufficient to turn on comparators 1–4 might correspond to the digital value that represents 4 volts. Turning on comparators 1–5 might correspond to 5 volts and so on. The resolution of this type of analog to digital converter is limited only by the number of comparators and the increment required to successively turn them on.

Traditional ADC's use the linear predictive coding ("LPC") technique which requires fewer parts to construct but requires more internal software to accomplish the ADC conversion. LPC ADC's are also significantly slower.

Flash ADC's are available from the Mountain Computer Corporation and other sources and are well known to those of ordinary skill in the art.

Figure 14:
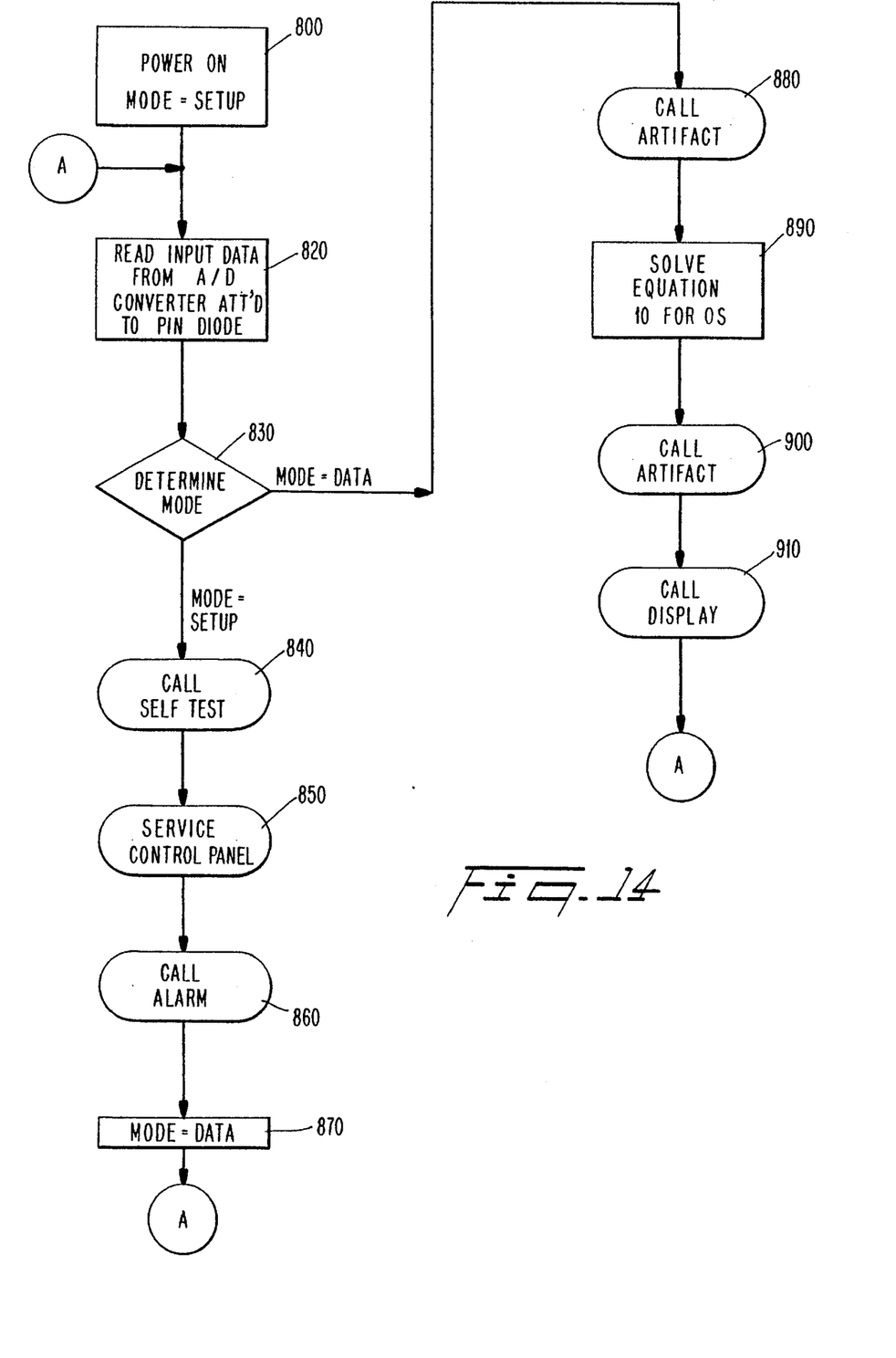
FIG. 14 is a flow chart of the software for the oximeter according to a preferred embodiment of the present invention.

The microprocessor 500 reads digitized data from flash analog to digital converter 340 and processes that data digitally in accordance with preprogrammed instructions as outlined in FIG. 14.

The processing sequence involves first measuring the electrical current changes that result from the backscattered laser light that impinges on PIN diode detector 210. The current is changed into a voltage that varies with time and then changed into a digital signal by flash analog to digital convertor 540. The incident beam center frequency also varies with time. The microprocessor 500 determines the frequencies that correspond to particular measured backscattered light intensities through reading one of the channels of the analog to digital converter 540 which provide a digital signal which varies with the ramp voltage as a function of time. Microprocessor 500 uses this indication of the state of the ramp voltage as a vector into a look-up table (contained in EPROM 510) to find the incident beam frequency which corresponds to each measured backscatter intensity. The quantities which are then available for solution of the general form of the equation for oxygen saturation ("OS") are: incident beam frequency as a function of time, and beam intensity as a function of time. The general form of the equation for oxygen saturation (as a function of multiple wavelengths) is:

$$OS = \frac{B(0) + B(1)\log R(1) + \ldots + B(n)\log R(n)}{A(0) + A(1)\log R(1) + \ldots + A(n)\log R(n)} \quad \text{(Equation 10)}$$

where:

B(0) and A(0) are empirically determined constants for the system.

A(1) through A(n) and B(1) through B(n) are empirically determined coefficients for the wavelengths in question.

and

R(1) through R(n) are the ratios of the intensities of the transmitted beams to the intensities of the backscattered beams at wavelengths lambda(1) through lambda(n), respectively.

The methodology for determining the values of the foregoing empirically determined constants and coefficients is well known to those of ordinary skill in the art and is set forth, for example, in U.S. Pat. No. 4,523,279 and "Influence of Oxygen Saturation, Erythrocyte Concentration and Optical Depth Upon Red and Near-Infrared Light Transmittance of Whole Blood", Kramer, K., Elam, J. O., Saxton, G. A., and Elam, W. N., Jr., *Chest*, Vol. 165, pp. 229–246 (1950). Copies of both of these references are submitted herewith.

After solving for the percent saturation, i.e., OS, the microprocessor 500 directs the digital output to a digital to analog converter 550. The analog voltage is then routed to a DVM circuit that reads the voltage and displays the decimal equivalent on a liquid crystal display (LCD). The variation in the ratio of the summed intensities is presented to the digital to analog converter 550. The resultant analog voltage is routed optionally to a bargraph LCD as an indication of the signal strength. Besides solution of the saturation equation, Microprocessor 500 contains software routines which perform the functions of: correction of various artifacts (such as movement), the setting and monitoring of alarm limits and the sounding of an alarm signal corresponding to the calculated value of OS exceeding the maximum alarm limit value or falling below the minimum alarm limit value.

In more detail, Microprocessor 500 that controls the oximeter of the present invention can be any microprocessor capable of performing the functions described herein. In a preferred embodiment, an INTEL 80386 microprocessor may be used, but others are appropriate as is well known to those of ordinary skill in the art. The physical system architecture of electronics module 220 is diagrammed in FIG. 13. Microprocessor 500 has address, data and control lines. EPROM 510 contains predetermined data such as the coefficients A(i) and B(i) of Equation 10 and the transmitted intensities at various preselected wavelengths of the laser device. RAM 520 is used for storage of data read during operation and for executing programs. ROM 530 is used for boot files and load executables. Flash analog to digital converter 540 obtains analog data from PIN diode detector 210 and from a ramp voltage supply (not shown) and provides digitized data reflecting the values of each at each clock cycle. Digital to analog converter 550 drives the various output devices indicative of the solved values of OS from Equation 10 and, optionally, other data desired such as pulse rate and pulse strength. These displays may be of the bargraph type, or, preferably, digital numerical displays such as LCD panels.

A ramp voltage supply (not shown) is supplied which provides a saw tooth waveform having a periodicity of less than or equal to approximately 30 microseconds. This supply may be implemented in any of a number of ways well known to those of ordinary skill in the art.

Depending upon the laser system used, the ramp supply may be adapted to be other than sawtooth in form depending upon what type of signal is useful in driving the periodic tuning circuit of the tuneable laser system selected. One of ordinary skill in the art may easily select an appropriate signal waveform and circuit for generating same with appropriate periodicity.

The value of 30 microseconds was selected to allow best possible resolution of the oxygen saturation value. The reason is simple: in a 30 microsecond interval there is a very low probability of micro changes in $O_2$ saturation. Therefore, it appears that all of the intensity ratios were taken at the same time, rather than at widely spaced intervals. The rapid repetition of frequencies also allows satisfaction of the principles of NYQUIST's theorem which states: "to accurately reproduce a waveform, one must sample the waveform at 2 times the highest frequency to be measured." Since 30 microseconds is significantly less than 1 second, the plethysmographic signal can be accurately reproduced.

Operation of the basic software which controls the oximeter of the present invention is straightforward. Turning to FIG. 14, a flowchart is provided. At power on 800 the "MODE" flag is set to "SETUP". Input data is read 820 from A/D converter providing PIN intensity and ramp voltage (and thereby indicating center frequency of transmitted light corresponding to the backscattered light intensity reflected by the PIN intensity reading). The mode is then determined 830 is checked and if in "DATA" mode, control transfers to call artifact 880. If the mode is "SETUP", the SELF TEST routine 840, SERVICE CONTROL PANEL ROUTINE 850 and 860 subroutines are called. Upon conclusion, the "MODE" flag is set to indicate "DATA" mode 870 and control transfers to again read input data 820.

SELF TEST ROUTINE 840 is a basic power-on self test routine which is well known to those of ordinary skill in the art.

SERVICE CONTROL PANEL ROUTINE 850 is a standard routine designed to service the controls available to the operator of the oximeter. Typical controls would include power on/off, set alarm level, test and the like. Operation is straightforward and known to those of ordinary skill in the art.

ALARM ROUTINE 860, discussed hereinbefore, is a subroutine which allows limit values of OS to be set so that if OS exceeds a maximum limit or falls below a minimum limit, an appropriate alarm sound will be generated allowing the doctor in attendance to be advised of the OS status. Operation is straight forward and known to those of ordinary skill in the art.

At call artifact 880, the ARTIFACT routine is called to process the raw data. ARTIFACT is described in more detail below.

Equation 10 (above) is 890 solved for OS as set forth above using predetermined data stored in EPROM 510 and measured data.

ARTIFACT is again called 900 to perform a check of the solved value of OS relative to certain parameters such as previous value, allowable values, and the like. If the solved value of OS is determined to be anomalous, it is thrown out and not displayed and further data is processed. If the solved value of OS is acceptable to ARTIFACT, then the display routine 910 is called to output the value of OS to, for example, an LCD display panel. Such techniques are well known to those of ordinary skill in the art and need not be described further herein.

ARTIFACT is a routine which cleans up the data. ARTIFACT corrects for movement of the probe, different tissue types/pigmentation, and noise in the signal. It also performs output data verification as previously described.

ARTIFACT operates in one of three modes at any given time. The first mode removes the dc direct current base line shift for a pulse train by constructing a pulse from data points and establishing the features of the pulse. The features are minimum and maximum amplitude of the pulse and the location of the dicrotic notch. All pulses thereafter are referenced (by their cardinal points) against the base line established for the first pulse.

The tissue type is achieved by knowing that certain wavelengths of light will vary in absorption due to specific tissue types of pigmentation. Certain other wavelengths will not vary for those same types and pigmentation. The Lambert-Beer equation is used to solve for tissue type in a manner similar to solving for saturated oxygen. The resolution of a specific tissue type is limited only by the number of wavelengths resolved (that vary and remain constant) and the amount of memory available to store the data.

Tissue type is determined by the ARTIFACT subroutine by relying on the fact that persons of certain racial groups absorb light at certain frequencies in different proportions than persons of other racial groups (These frequencies also happen to be unaffected by the blood volume pulse.) Therefore when scanning (tuning) the laser, we look at the aforementioned frequencies (available in the literature) and determine the percent absorption and match the ratio to the racial group which most closely corresponds. When a match is found between the absorption profile and a particular racial group, the A(o) and B(o) constants (for Equation 10) associated with the racial group are retrieved from the EPROM (look-up) tables and substituted into Equation 10 for oxygen saturation.

The methodology for measuring the A and B values is widely known throughout the medical field and is described, for example, in Takatani's 1980 paper "A Non-Invasive Tissue Reflectance Oximeter", supra.

Removal of noise is achieved via digital filtering techniques that are well understood in the industry. A high level description would be the equivalent of doing multiple least squares curve fits until the most logical waveform results for display to the user.

Tuneable Lasers

1. Titanium Doped Sapphire Paramagnetic Ion Laser

Figure 9:
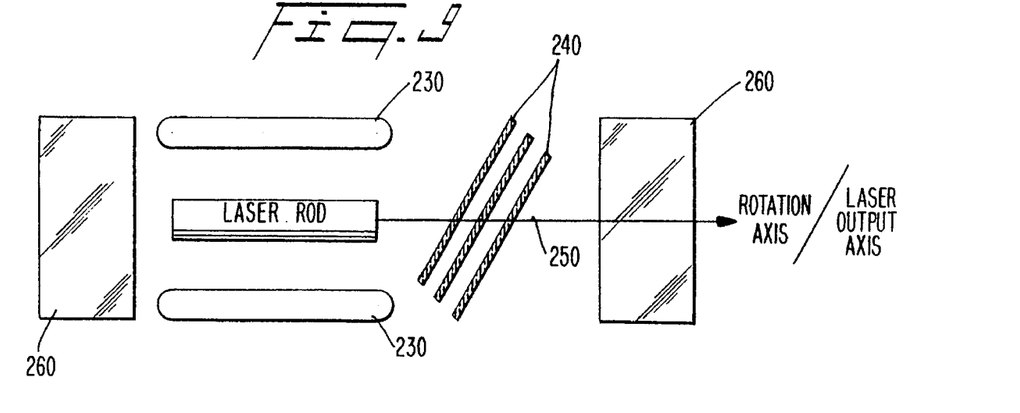
FIG. 9 is a schematic diagram of a tuneable titanium doped sapphire laser according to a first preferred embodiment of the present invention.

In a preferred embodiment of the present invention shown in FIG. 9, the Titanium doped Sapphire laser utilizes the high voltage output from the electronics module (not shown) to power the Argon pump sources 230 to achieve a population inversion (lasing). Mirrors 260 define the laser cavity. The tuning is achieved via rotation of the birefringent crystals 240 (using the ramp voltage to drive a stepper motor) in their own plane about laser axis 250. This rotation changes the included angle between the birefringent crystal optical axis and the laser axis 250 and, hence, the effective principal refractive indices of the crystal. It is to be noted that the output of a laser such as this is linearly polarized without the addition of an additional polarizing element such as a Brewster window.

The resultant wavelength LAMBDA is given by:

$$\text{LAMBDA} = \frac{2\pi h(\eta_o - \eta_E)\sin^2\Theta}{\delta \sin\alpha} \quad \text{(Equation 11)}$$

Where:

$\delta$ is the phase difference between the ordinary and extraordinary rays emerging from the crystal.

$\alpha$ is the angel of incidence.

and $\Theta$ is the angle between the plane of incidence and the crystal optical axis.

2. Progressively Doped Two Dimensional Laser Diode Array

Figure 10A:
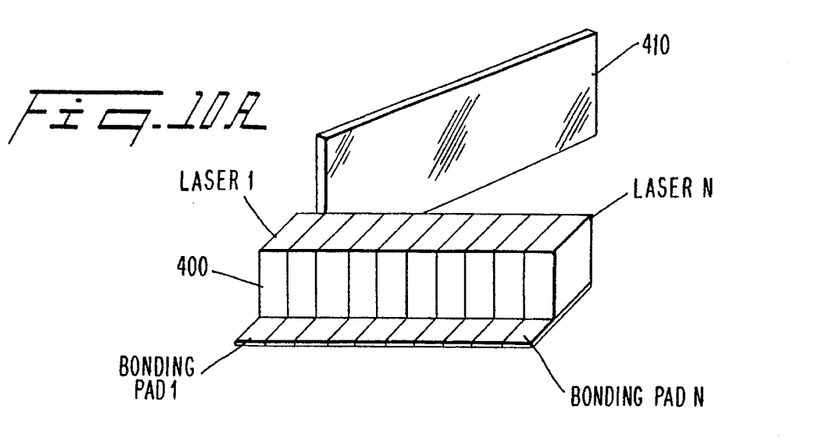
FIG. 10A is a schematic diagram showing a first view of a tuneable progressively doped laser diode array according to a second preferred embodiment of the present invention.
Figure 10B:
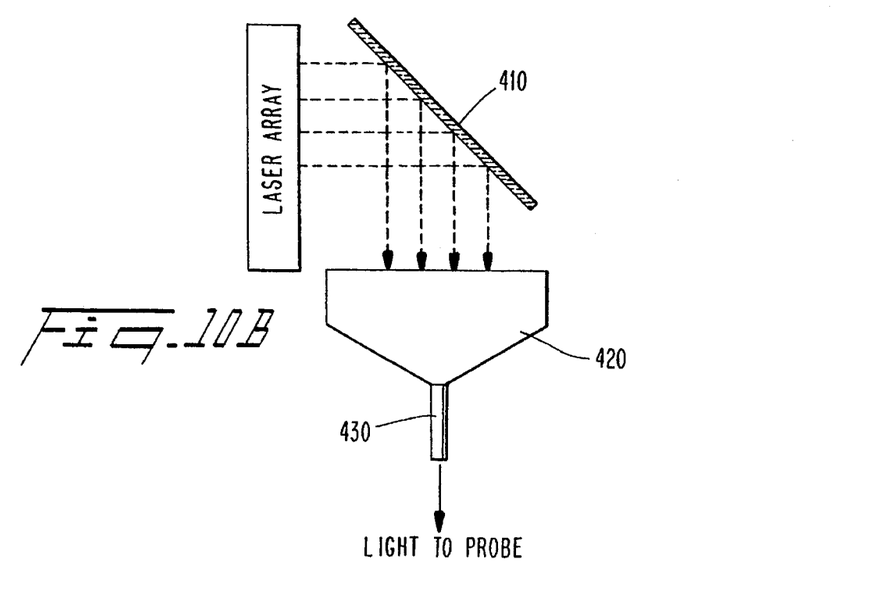
FIG. 10B is a second view of the tuneable progressively doped laser diode array of FIG. 10A.

The progressively doped two dimensional array shown in FIGS. 10A and 10B consists of several laser diodes 400 stacked such that the ramp voltage (when applied to a comparator circuit) causes the diodes to be sequentially lighted. The light from the diodes is directed via a front surfaced mirror 410 into a beam combiner 420 and the light from the combiner is directed out of the LASER assembly via a fiber light pipe 430. The construction of the array begins by subassembling individual laser devices that have been progressively doped such that their combined frequencies cover the band of interest. The doping process starts by growing layers of AlGaAs on a GaAs substrate using MOCVD. These layers serve to provide carrier and optical confinement to achieve good lasing efficiency. Next the stripe-laser patterns are produced photolithographically and the contact metalizations are deposited. The laser cavity mirrors for the individual devices result from the die cleaving process. The back facets are coated with a dielectric coating to prevent light loss. Wire bonding pads for the individual devices are formed from the spacers separating the individual devices. The inventor is advised that devices such as that described herein are available from the Advanced Micro Devices (AMD) Company of Sunnyvale, Calif.

3. Tuneable Double Heterostructure Diode Laser

The tuneable double heterostructure laser operation takes advantage of the instability of the emission frequency as a function of temperature. The diode is surrounded by the equivalent of a crystal oven whose temperature varies as a function of the applied ramp voltage. Such devices are capable of output frequency changes as a function of applied voltage. At the present time the inventor is advised that double heterostructure semiconductor diodes are available from the McDonnel Douglas Corporation.

4. Selectable Fixed Frequency Dye Laser

Figure 11:
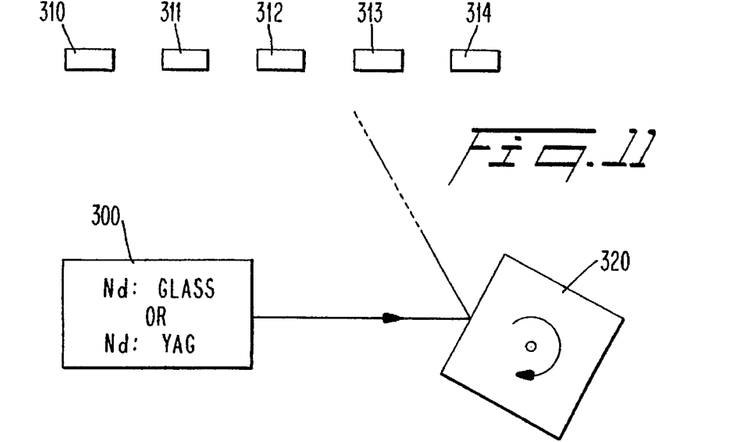
FIG. 11 is a schematic diagram of a selectable fixed frequency dye laser.

This configuration of laser is diagrammed briefly in FIG. 11. A Nd:glass or Nd:YAG laser in frequency doubled configuration 300 is used as a pump source for a plurality of dye laser cells 310, 311, 312, 313, 314. Each dye laser 310–314 is constructed to lase at a different frequency in the approximate range of 600 nM to 1000 nM when excited by the output of laser 300. A rotating mirror or polyhedron 320 or other suitable scanning device directs the exciting energy to cells 310–314 sequentially. Synchronization to ramp voltage signal can be provided by synchronizing the motor driving mirror 320 to the ramp voltage signal so that Microprocessor 500 can determine the cell selected at any given moment.

5. Tuneable Raman Scattered Laser

Figure 12:
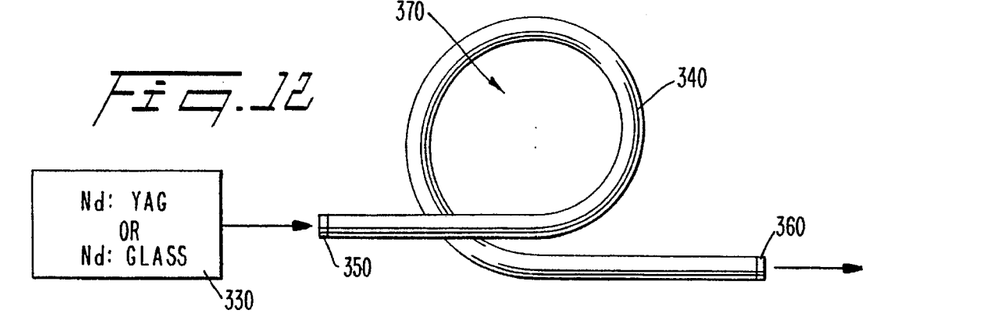
FIG. 12 is a schematic diagram of a tuneable Raman scattered laser.

In this system a single adjustable or series of fixed fiberoptic cables 340 are doped with a semiconductor compound such that the cables 340 are capable of lasing over a fairly wide bandwidth of frequencies. The cable 340 is then end pumped with a frequency-doubled Nd:YAG or Nd:glass laser 330 as shown in FIG. 12. To achieve the tuning capability a loop 370 is placed in cable 340 as shown. The stresses in cable 340 cause its index of refraction to vary as a function of how tight the loop 370 in cable 340 is. Hence the center frequency of the emitted laser light is adjustable as a function of the size of loop 370. Given this property either a series of fixed looped cables can be created, each tuned to a particular desired frequency, or the cable loop can be adjusted mechanically as a function of the ramp voltage. In the multi-cable embodiment, particular cables can be selected for light output through use of an LCD shutter, a rotating aperture wheel, or similar device synchronized to the ramp voltage signal. In this embodiment, first surface 350 should admit light in the range of approximately 500 nM but should be highly reflective in the range of 600–1000 nM. Second surface 360 should be about 90% reflective in the 600–1000 nM range.

I claim:

1. An apparatus for measuring the oxygen content of blood within a patient comprising:

a light source for transmitting an incident beam with a linearly polarized, monochromatic light having a first amplitude;

a directional coupler having a first port, a second port, and a third port, said second port optically coupled to said light source;

an optical fiber coupled to the third port of said directional coupler;

an optical coupler coupled to said optical fiber for interfacing between said optical fiber and said patient, with said optical coupler including a flat optical glass for flattening an underlying capillary bed of skin of said patient, thereby presenting a flat surface area perpendicular to said optical fiber, with the incident beam passing through the second port and the third port of said directional coupler, through said optical fiber and said optical coupler, to the underlying capillary bed, with a portion of the incident beam reflecting from the underlying capillary bed as a reflected beam, with the reflected beam passing from said optical coupler, through the optical fiber, through the third port and out the first port of said directional coupler;

a polarizing filter coupled to said first port for filtering the reflected beam with linear polarization and for passing the reflected beam having a 180 degree phase shift with respect to the incident beam;

a detector optically coupled through said polarizing filter to the first port of said directional coupler for measuring a second amplitude of the reflected beam having a 180 degree phase shift with respect to the incident beam, with the reflected beam passing from said underlying capillary bed through the optical coupler, through the third port of said directional coupler, through the first port of said directional coupler, and through said polarizing filter; and processing means, electrically coupled to said light source and to said detector, for receiving the first amplitude from the light source and the second amplitude from the detector, said processing means having a data table summarizing blood oxygen values and comparing the first amplitude with the second amplitude and, referencing the data table, determining a value indicating a quantity of oxygen in the blood.

2. An apparatus for spectrophotometrically measuring and displaying an oxygen content of blood within a living patient comprising:

a tuneable laser source for generating a plurality of light signals as an incident beam having a measured intensity, each of said plurality of light signals being coherent, linearly polarized and monochromatic;

a directional coupler having a first port, a second port and a third port, said first port optically connected to a polarizing filter and a detector, said second port optically conected to said tuneable laser source, and said third port optically connected through an optical fiber to the patient;

means coupled to the optical fiber and adapted for directing the incident beam through the optical fiber into the patient, non-invasively and transcutaneously along a path, with the optical fiber perpendicular to an underlying capillary bed of skin of the patient;

means coupled to the optical fiber and adapted for directing backscattered radiation generated within the patient in response to said incident beam along said path as a reflected beam to said first port, said polarizing filter and said detector;

said polarizing filter for filtering the reflected beam with linear polarization and for passing the reflected beam having a 180 degree phase shift with respect to the incident beam as a 180-degree-phase-shifted-reflected beam;

said detector adapted to measure an intensity of the 180-degree-phase-shifted-reflected beam; and calculating means, electrically coupled to the detector and to the tuneable laser source, having a data table summarizing blood oxygen values and responsive to receiving and comparing the measured intensity of the incident beam and the intensity of the 180-degree-phase-shifted-reflected beam, for determining and displaying the oxygen content of blood.

3. The apparatus of claim 2 with said different wavelengths are in the range of plurality of light signals being in a range from 600 to 1000 nanometers.

4. The apparatus of claim 2 with said tuneable laser source consisting essentially of a single tuneable laser generating said plurality of light signals sequentially.

5. The apparatus of claim 4 including means for sweeping said plurality of light signals every 30 microseconds.

6. The apparatus of claim 2 with said detector including a PIN diode.

7. The apparatus of claim 6 with said tuneable laser source consisting essentially of a single tuneable laser generating said plurality of light signals sequentially.

8. The apparatus of claim 7 including means for sweeping said plurality of light signals every 30 microseconds.

9. An apparatus for spectrophotometrically measuring and displaying information related to a quantity present of a preselected constituent of a living patient's blood comprising:

a solid state laser tuneable in the range of about 600 nm–1000 nm for generating a plurality of light signals as an incident beam, each of said plurality of light signals being coherent, linearly polarized and monochromatic;

a directional coupler having a first port, a second port, and a third port, said first port optically coupled to a linear polarizing filter oriented 180° out of phase with polarization of said incident beam, said first port also optically coupled to a PIN diode detector, said second port optically coupled to said laser, and said third port optically coupled through an optical fiber to the patient;

means coupled to the optical fiber and adapted for directing said incident beam along a path through the optical fiber into the patient, non-invasively and transcutaneously, with the optical fiber perpendicular to an underlying capillary bed of skin of the patient;

means coupled to the optical fiber and adapted for directing backscattered radiation, generated within the patient in response to said incident beam, back along said path as a reflected beam to said first port, said linear polarizing filter and said PIN diode detector;

said linear polarizing filter for filtering the reflected beam with linear polarization and for passing the reflected beam having a 180 degree phase shift with respect to the incident beam as a 180-degree-phase-shifted-reflected beam;

said PIN diode detector adapted to measure an intensity of said 180-degree-phase-shifted-reflected beam; and calculation means, electrically coupled to said laser and to said PIN diode detector, for receiving and comparing an intensity of the incident beam and the intensity of the 180-degree-phase-shifted-reflected beam, said calculation means having a plurality of data tables summarizing quantities of a plurality of constituents of blood, respectively, said calculation means for referencing a particular data table summarizing the preselected constituent and for determining and displaying, using the intensity of the incident beam and the intensity of the 180-degree-phase-shifted-reflected beam, a value indicating a quantity of the preselected constituent in the blood.

10. The apparatus of claim 9 including means for sweeping said plurality of light signals every 30 microseconds.

11. The apparatus of claim 9 with said solid state laser including means for generating said plurality of light signals sequentially.

12. A spectrophotometric method for transcutaneously and non-invasively determining an oxygen content of blood within a living patient, using a tunable laser source capable of producing monochromatic light at a multiplicity of frequencies, a directional coupler, a polarizing filter, a detector, an optical fiber, an optical coupler, and a processor, the method comprising the steps of:

generating, using the tunable laser source, a plurality of light signals having wavelengths within the range of about 600 nm to about 1000 nm as an incident beam, each of said plurality of light signals being coherent, linearly polarized and monochromatic;

applying said incident beam to the directional coupler, the directional coupler having a first port, second port and a third port, said first port optically coupled to the linear polarizing filter oriented 180° out of phase with the polarization of said plurality of light signals, said first port of said directional coupler also coupled to the detector, said second port optically coupled to said tunable laser source, and said third port optically coupled, through the optical fiber and the optical coupler, to the patient;

directing the incident beam into the patient non-invasively and transcutaneously along an optical path;

directing backscattered radiation, generated within the patient in response to said incident beam, as a reflected beam back along said optical path to said third port, through said first port, and to said linear polarizing filter;

filtering, by said polarizing filter, said reflected beam and passing a portion of the reflected beam having a 180 degree phase shift with respect to said incident beam to said detector as a 180-degree-phase-shifted-reflected beam;

measuring, by the detector, an intensity of said 180-degree-phase-shifted-reflected beam;

comparing, by the processor, an intensity of said incident beam and the measured intensity of said 180-degree-phase-shifted-reflected beam;

referencing, by the processor, a data look up table summarizing blood oxygen values;

calculating, using the comparison and the reference, an oxygen content of blood; and displaying the oxygen content of blood.

13. A spectrophotometric method for transcutaneously and non-invasively determining an oxygen content of blood within a living patient, using a tunable laser source capable of producing monochromatic light at a multiplicity of frequencies; a directional coupler, optically coupled to said tunable laser source, having a first port, a second port and a third port; a polarizing filter, optically coupled to said first port; a detector, optically coupled to said first port; an optical fiber, optically coupled to said third port; an optical coupler, optically coupled to said optical fiber and perpendicular to said optical fiber; and a processor, electrically coupled to said tunable laser source and to said detector, the method comprising the steps of:

generating, with said tunable laser source, a plurality of light signals as an incident beam in the range of 600 nm–1000 nm, each of said plurality of light signals being coherent, polarized and monochromatic;

transmitting a first amplitude of said incident beam to said processor;

applying said incident beam to the second port of said directional coupler;

optically conveying said incident beam out the third port of said directional coupler, through said optical fiber, to said optical coupler;

directing the incident beam into the patient non-invasively and transcutaneously along a path;

directing backscattered radiation, generated within the patient in response to said incident beam, along said path as a reflected beam to said third port and out said first port;

filtering with linear polarization, by said polarizing filter, said reflected beam and passing a portion of the reflected beam having a 180 degree phase shift with respect to said incident beam as a 180-degree-phase-shifted-reflected beam;

detecting, by said detector, the 180-degree-phase-shifted-reflected beam;

measuring a second amplitude of the 180-degree-phase-shifted-reflected beam;

transmitting the second amplitude to said processor;

comparing, by said processor, the first amplitude and the second amplitude;

referencing, by said processor, a data look up table;

calculating, using the comparison of the first amplitude and the second amplitude, and the data look up table, an oxygen content of blood; and displaying the oxygen content of blood.

14. The method of claim 13 further comprising the step of sweeping said plurality of light signals every 30 microseconds.

* * * * *